(12) United States Patent
Drakulic

(10) Patent No.: US 7,299,083 B2
(45) Date of Patent: Nov. 20, 2007

(54) ELECTRODE FOR, AND METHOD OF, INDICATING SIGNAL CHARACTERISTICS AT PARTICULAR POSITIONS IN A PATIENT'S BODY

(75) Inventor: Budimir Drakulic, Los Angeles, CA (US)

(73) Assignee: Signalife, Inc., Studio City, CA (US)

( * ) Notice: Subject to any disclaimer, the term of this patent is extended or adjusted under 35 U.S.C. 154(b) by 377 days.

(21) Appl. No.: 11/008,681

(22) Filed: Dec. 9, 2004

(65) Prior Publication Data

US 2006/0129042 A1 Jun. 15, 2006

(51) Int. Cl.
*A61B 5/04* (2006.01)

(52) U.S. Cl. .................. 600/372; 600/396; 600/397; 128/902

(58) Field of Classification Search .............. 600/372
See application file for complete search history.

(56) References Cited

U.S. PATENT DOCUMENTS

| | | |
|---|---|---|
| 4,200,109 A | 4/1980 | McMorrow, Jr. |
| 4,204,546 A | 5/1980 | Smith et al. |
| 4,263,561 A | 4/1981 | Weber |
| 4,608,987 A | 9/1986 | Mills |
| 4,610,259 A | 9/1986 | Cohen et al. |
| 4,679,568 A | 7/1987 | Blau et al. |
| 4,803,996 A | 2/1989 | Peel et al. |
| 4,924,875 A | 5/1990 | Chamoun |
| 4,928,704 A | 5/1990 | Hardt |
| 5,038,782 A | 8/1991 | Gevins et al. |
| 5,263,487 A | 11/1993 | Sakamoto et al. |
| 5,275,172 A | 1/1994 | Ives |
| 5,368,041 A | 11/1994 | Shambroom |
| 5,513,649 A | 5/1996 | Gevins et al. |
| 5,678,559 A | 10/1997 | Drakulic |
| 6,496,705 B1 | 12/2002 | Ng et al. |
| 6,546,281 B1 | 4/2003 | Zhang et al. |
| 6,549,804 B1 | 4/2003 | Osorio et al. |
| 6,597,942 B1 | 7/2003 | Yonce |
| 6,681,003 B2 | 1/2004 | Linder et al. |
| 6,726,673 B1 | 4/2004 | Zhang et al. |
| 6,772,004 B2 | 8/2004 | Rudy |
| 6,823,209 B2 | 11/2004 | Olson et al. |
| 2004/0265353 A1 | 12/2004 | Zhang et al. |

FOREIGN PATENT DOCUMENTS

| | | |
|---|---|---|
| CA | 2324713 | 10/2000 |
| EP | 0486399 | 5/1992 |
| EP | 1275342 A2 | 7/2001 |

*Primary Examiner*—Lee S. Cohen
(74) *Attorney, Agent, or Firm*—Fulwider Patton LLP

(57) ABSTRACT

A chadd disposed on a patient's skin generates heat at a substantially constant temperature for an extended period of time (e.g., hours and days) when exposed to air. The chadd becomes porous when heated and produces a porosity in the patient's skin as a result of the heat generation to pass ions through the pores in patient's skin to a layer disposed on the chadd. The layer (e.g., silver or silver chloride) has properties of converting the ions to electrons. The electrons pass to an electrical lead disposed on the layer. The electrical lead passes an electrical signal (produced from the electrons) to a terminal. An amplifier connected to the terminal amplifies the signal without changing the characteristics of the signal and without producing noise.

56 Claims, 4 Drawing Sheets

US 7,299,083 B2

ELECTRODE FOR, AND METHOD OF, INDICATING SIGNAL CHARACTERISTICS AT PARTICULAR POSITIONS IN A PATIENT'S BODY

This invention relates to a system for, and method of, producing at a particular position on the patient's body, signals having characteristics indicating the functioning of the patient's body at the particular position. The invention is particularly adapted to being used for monitoring a patient's heart.

BACKGROUND OF A PREFERRED EMBODIMENT OF THE INVENTION

Measurements are provided in a patient of the functioning of various organs in a patient's body. For example, measurements are made of the functioning of the patient's heart and the patient's brain. These measurements are generally made by applying an electrode or electrodes to the skin of the patient at the appropriate position or positions in the patient's body and by evaluating the characteristics of the signal produced at the particular position or positions.

The measurements of the functioning of different organs in the patient's body involve different frequency ranges. For example, measurements of the patient's heart occur in a range of DC to approximately two hundred fifty hertz (250 Hz) and measurements of the patient's brain occur in a range of DC to approximately one hundred and fifty hertz (150 Hz).

The measurement of the functioning of different organs in the patient's body involves acquiring signals of miniscule amplitudes. For example, the range of voltages produced at an electrode attached to the patient's skin for a measurement of the patient's heart is approximately one-half of a millivolt (0.5 mV) to approximately four millivolts (4 mV). The range of voltages produced at an electrode attached to the patient's skin for a measurement of the patient's brain is approximately five microvolts (5 µV) to approximately three hundred microvolts (300 µV).

When an electrode is attached to the patient's skin to measure the function of an organ such as the patient's heart or brain, the bioelectric signal generated from the organ has to penetrate from the patient's organ through the body to the patient's skin and to the electrode attached to the patient's skin. The patient's skin has many layers. The greater the number of layers that the signal has to penetrate in the patient's skin, the greater is the impedance and barrier that the skin presents to the signal generated by the organ whose function is being measured. The problem of high impedances is compounded if the patient's skin is not clean and prepared by abrading when the measurement is being made. Thus, the impedance presented by the patient's skin may be as high as approximately several thousand ohms to approximately several hundred thousand ohms. The input impedance of the recording amplifier connected to the electrode is preferably very high so as not to alter the characteristics of the original signal.

BRIEF DESCRIPTION OF A PREFERRED EMBODIMENT OF THE INVENTION

A chadd disposed on a patient's skin generates heat at a substantially constant temperature for an extended period of time (e.g. hours and days) when exposed to air. The chadd becomes porous when heated and produces a porosity in the patient's skin as a result of the heat generation to pass ions through pores in the patient's skin to a layer disposed on the chadd. The layer (e.g., silver/silver chloride) (Ag/AgCl) has properties of converting the ions to electrons. The electrons pass to an electrical lead disposed on the layer. The electrical lead passes an electrical signal (produced from the electrons) to a terminal. An amplifier connected to the terminal amplifies the signal without changing the characteristics of the original signal and without producing noise.

DETAILED DESCRIPTION OF A PREFERRED EMBODIMENT OF THE INVENTION

Figure 3:
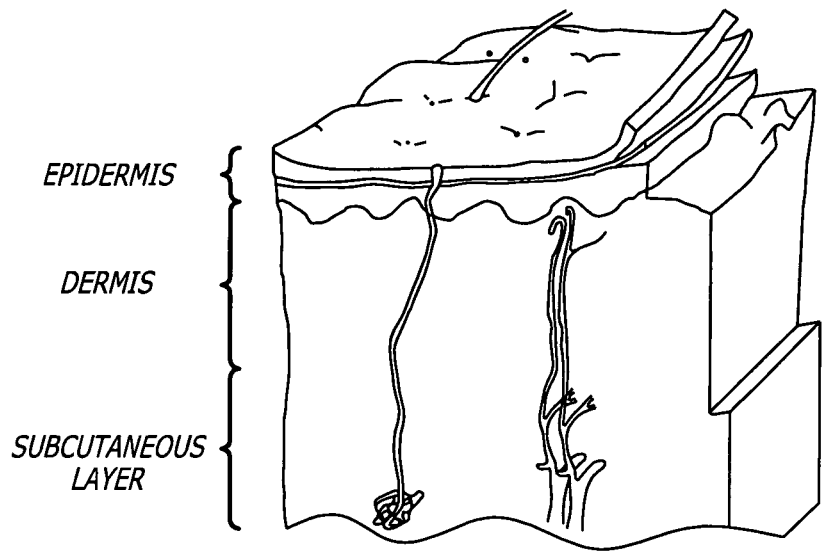
FIG. 3 is a schematic perspective view of the different layers in a patient's skin.

FIG. 3 is an enlarged schematic perspective view of the different layers in a patient's skin. As will be seen, there are a number of layers in the patient's skin. The bracketed indications on the left of FIG. 3 represent groupings of layers. These bracketed groupings of layers are respectively designated as epidermis, dermis and subcutaneous. Each of the layers includes a plurality of sub-layers.

Figure 4:
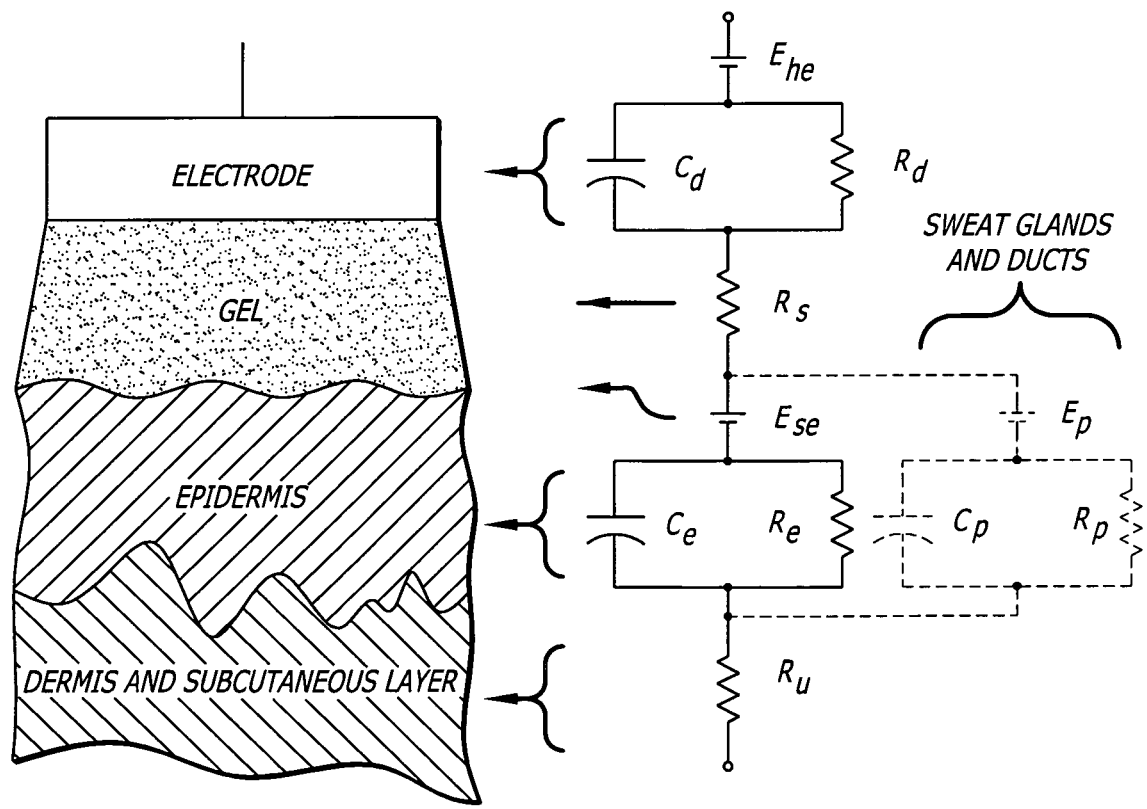
FIG. 4 is a simplified elevational view of an electrode, a patient's skin (on a simplified basis) and a gel for facilitating the coupling between the electrode and the patient's skin and also shows the impedance network formed by the electrode, the gel and the patient's skin.

Each of the layers in FIG. 3 has an impedance. This is shown on a schematic basis in FIG. 4 which shows an arrangement in the prior art for attaching an electrode to a patient's skin. The showing in FIG. 4 includes an electrode, a gel, the epidermis layer and a combination of the dermis and subcutaneous layers. In FIG. 4, the gel is shown as being disposed between the electrode and the epidermis to facilitate the coupling of the electrode to the epidermis layer with a minimal impedance.

Since each of the layers and sub-layers in the patient's skin has an impedance, the impedance of the patient's skin may be in the order of approximately several hundred thousand ohms when all of the layers are in place on the patient's skin. This high impedance limits the ability to create an electrical signal of any significant amplitude on the electrode.

It has previously been determined in the prior art that heat applied to a patient's skin increases the skin permeability, thereby allowing drugs to permeate the skin more efficiently and effectively than other methods previously used to introduce drugs into a patient's body.

In recent years, heat has been used to facilitate the insertion and penetration of drugs by transdermal delivery into a patient's body through the patient's skin. The insertion and penetration of drugs through a patient's skin by the application of heat to the patient's skin is advantageous in that the patient's skin does not have to be broken and no instrument has to puncture the patient's skin.

Heat initiates several physiological responses that facilitate drug penetration through the skin, including:

1. An increase in skin permeability. The increase in skin permeability provides for an enhanced flow of the drugs through the skin into the patient's body;

2. An increase in body fluid circulation. The increase in body fluid circulation enhances the rate at which the fluid travels through the patient's body;

3. Dilation of blood vessels. This enhances permeation of the drugs through the blood vessel wall;

4. An enhancement in the solubility of most drugs. This enhancement in drug solubility increases the rate at which the drugs can pass through the patient's body; and 5. An increase in the release rate of the drugs from local skin tissue into systemic circulation.

A number of patents have been obtained by Zars, Inc. of Salt Lake City, Utah on a system for, and method of, inserting drugs through a patient's skin into a patient's body. These include the following: U.S. Pat. Nos. 5,658,583; 5,919,479; 6,245,347; 6,261,595; 6,488,959; 6,528,086; and 6,546,281. All of these patents may be considered to be references of the prior art.

Figure 1:
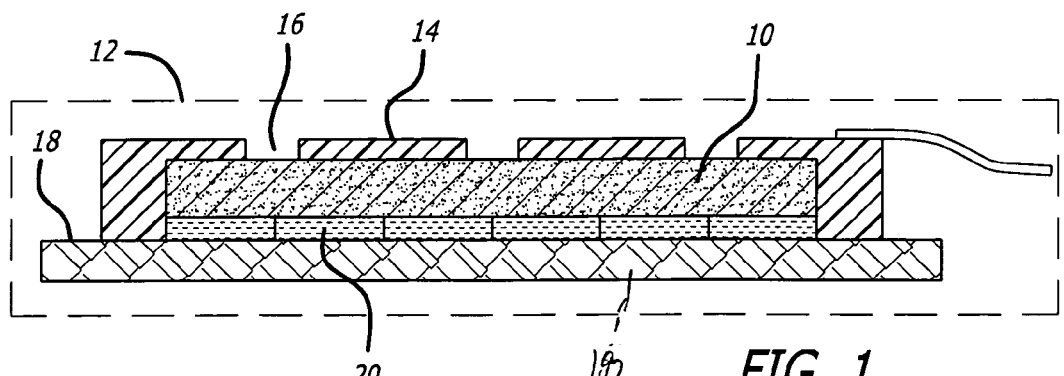
FIG. 1 is a front elevational view in section of a prior art embodiment for generating heat to introduce drugs into a patient's body.

In these patents, a chadd 10 in FIG. 1 is made from an oxidizable material. For example, the chadd 10 may be made from a mixture of activated carbon, iron powder, sawdust, sodium chloride and water. The activated carbon, iron powder, sawdust and water may be provided in the mixture in the relative ratios of 5:16:3:2: and 6.

The chadd 10 may ordinarily be disposed in a wrapper 12 to prevent air from being introduced to the chadd. A cover 14 with openings 16 is disposed between the wrapper 12 and the chadd 10. When the wrapper 12 is removed from the chadd 10, the cover 14 becomes exposed and the openings 16 in the cover 14 cause air to be introduced to the chadd. The oxygen in the air oxidizes the chadd 10 to generate heat in the chadd and to make the chadd porous. The heat in the chadd produces heat in the patient's skin 18. The heat in the chadd opens the pores in the patient's skin 18 and causes drugs 20 to pass through the pores in the patient's skin 18 into the patient's body. The drugs 20 are disposed in a layer between the chadd 10 and the patient's skin 18.

The temperature on the chadd 10 increases substantially instantaneously to a particular value when the chadd receives the air through the openings 16 in the cover 14. The particular value of the raised temperature of the chadd 10 is dependent upon the number and size of the openings 16 in the cover 14. The substantially instantaneous increase in the temperature of the chadd 10 to the particular value is indicated at 24 in FIG. 2. The chadd 10 is then maintained at the particular temperature for extended periods of time such as in the order of a full day or as many as fifteen (15) days. This is indicated at 26 in FIG. 2. During this extended period of time, the drugs 20 are delivered through the patient's skin into the patient's body.

Figure 2:
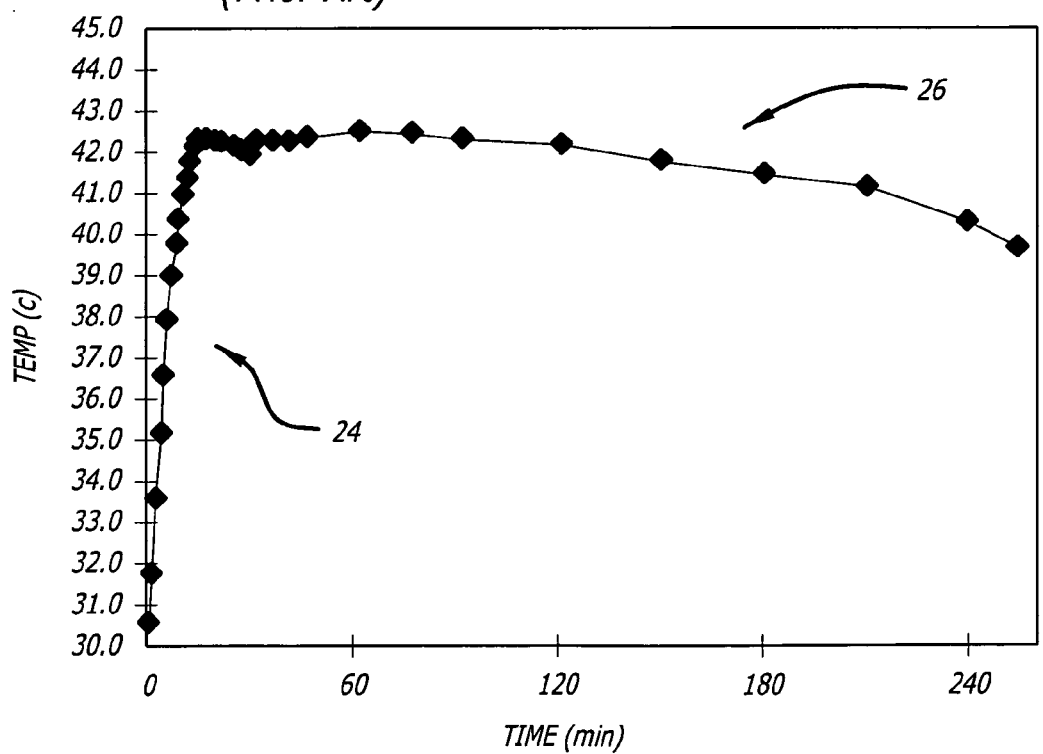
FIG. 2 is a graph showing time on a horizontal axis and temperature on a vertical axis and showing the substantially constant temperature generated by the prior art embodiment of FIG. 1 over an extended period of time.

As will be seen from the above discussion and from FIGS. 1 and 2, the drugs 20 enter into the patient's skin in the prior art as a result of heat applied to the patient's skin by the chadd 10. In applicant's invention, however, ions from the patient's body pass through the patient's skin to a position external to the patient's skin as in the prior art. This is in a direction opposite to the passage of the drugs 20 into the patient's body through the patient's skin 18. The ions in applicant's invention provide an indication of the characteristics of the patient's body at a particular position in the patient's body such as functioning of at the heart of a patient.

Figure 5:
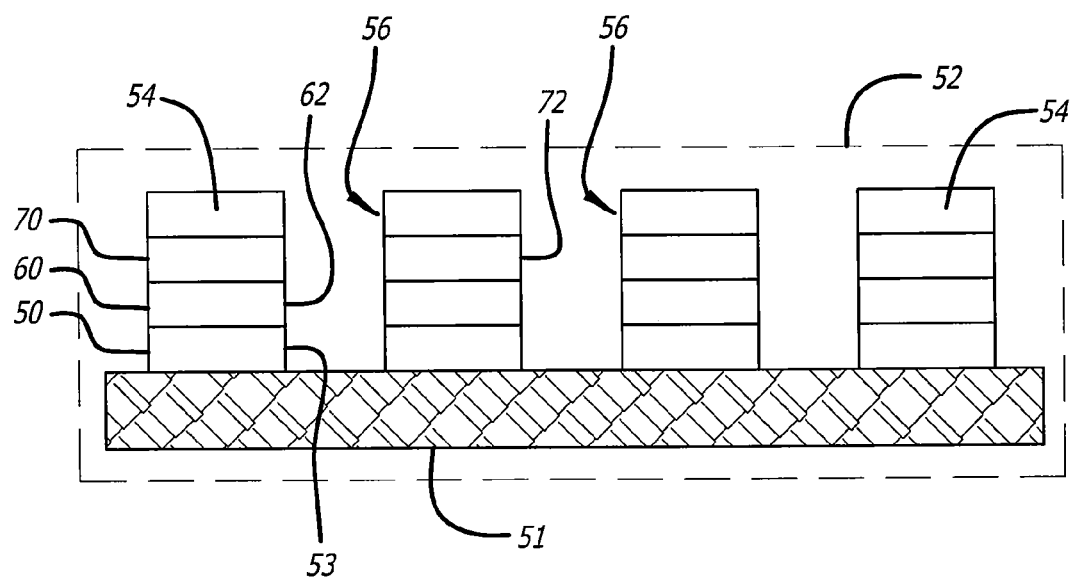
FIG. 5 is a schematic elevational view in section of a preferred embodiment of the invention for producing signals representing the characteristics of a patient's body at a particular position in the patient's body such as signal originated from- the-patient's heart.
Figure 6:
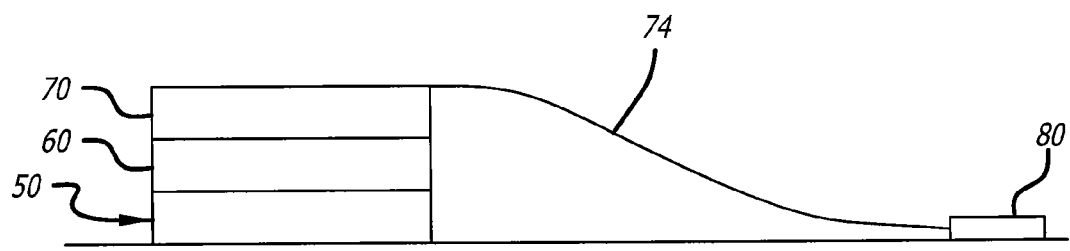
FIG. 6 is a schematic elevational view of the preferred embodiment of the invention.

In a preferred embodiment of applicant's invention, a chadd generally indicated at 50 in FIGS. 5 and 6 is attached to a patient's skin 51 at a particular position on a patient's body. This particular position may be an individual one of a plurality of different anatomical positions on the torso that enable an evaluation of the functioning of the patient's heart. The chadd 50 in FIG. 5 may have a construction corresponding to the construction of the chadd 10 in FIG. 1 and described above. This may include openings 53 in the chadd 50. A wrapper 52 corresponding to the wrapper 12 in FIG. 1 envelopes the chadd 50 and prevents the chadd from being oxidized. A cover 54 may be disposed within the wrapper 52. Openings 56 may be provided in the cover 54 to provide for the oxidation of the material in the chadd 50. The openings 56 may correspond to the openings 16 in the cover 14 in FIG. 1.

The chadd 50 in FIGS. 5 and 6 may be made from an oxidizable material corresponding to the oxidizable material in the chadd 10 in FIG. 1. Specifically, the chadd 50 in FIGS. 5 and 6 may be made from a mixture of activated carbon, iron powder, sawdust, sodium chloride and water. As with the chadd 10 in FIG. 1, the activated carbon, iron powder, sawdust, sodium chloride and water in the chadd 50 in FIGS. 5 and 6 may be provided in the mixture in the relative ratios of 5:16:3:2: and 6.

A layer 60 of an electrically conductive material may be suitably attached to the chadd 50 in FIGS. 5 and 6. The layer 60 may be made from a suitable material such as silver/silver chloride (Ag/AgCl). The layer 60 may be provided with openings 62 corresponding in position and in size to the position and size of the openings 53 in the chadd 50. An electrical lead 70 is attached to the layer 60. The electrical lead 70 may be provided with openings 72 corresponding in position and size to the openings 62 in the layer 60 and to the openings 53 in the chadd 50. The electrical lead 70 may be made from a suitable electrically conductive material such as an electrically conductive carbon or an electrically conductive plastic material such as an electrically conductive polyurethane.

The cumulative thickness of the chadd 50, the layer 60 and the electrical lead 70 may be in the order of approximately two millimeters (2 mm). The openings 62 in the layer 60 and the openings 72 in the electrical lead 70 assure that the air will flow into the openings 53 in the chadd 50 and that the oxygen in the air will oxidize the mixture of the material in the chadd to increase the temperature of the chadd instantaneously and therefore increase the temperature of the conductive layer 60. The relationship between temperature and time in the chadd 50 corresponds to that shown in FIG. 2.

When the chadd 50 is heated, it enables pores to open in the patient's skin 51 and in the chadd. This causes ions to pass through the pores in the patient's skin 51 and in the chadd from the particular positions in the patient's body. These ions pass to the layer 60 which reacts chemically with the ions to produce electrons. The electrons produce an electrical signal in the electrical lead 70. The electrical signal indicates the characteristics of the patient's heart at the particular position.

An extension 74 of the electrical lead 70 extends to a terminal 80. The extension 74 may be in the form of a single strand or may be in the form of a tape. The extension 74 is connected to an amplifier generally indicated at 100 in FIG. 7.

Figure 7:
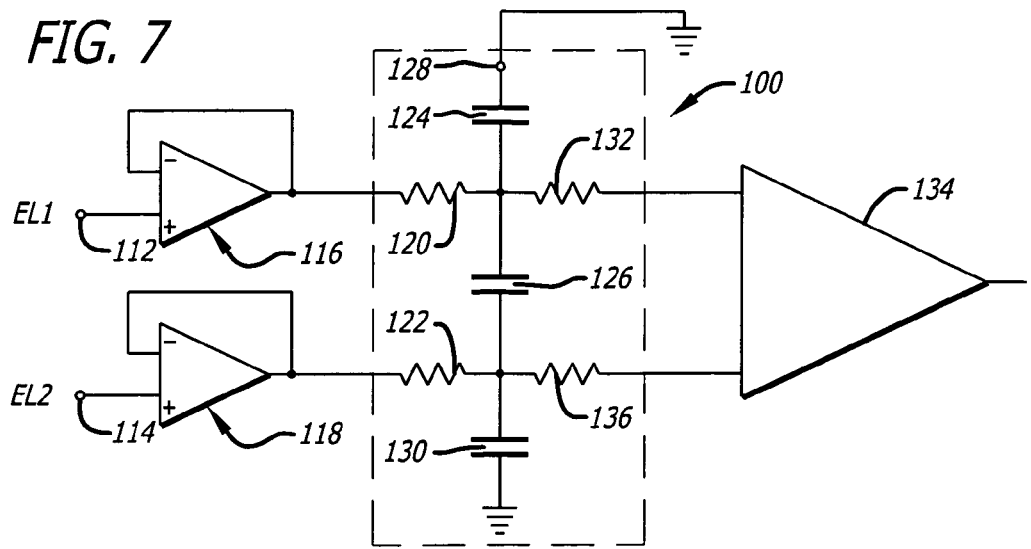
FIG. 7 is a circuit diagram, substantially in block form, of an amplifier system, including a pair of amplifiers and a pair of electrodes for amplifying low-amplitude signals produced by the patient's heart without affecting the characteristics of the signals and without introducing noise into the signals.

FIG. 7 is a circuit diagram, primarily in block form, of the amplifier 100 included in a preferred embodiment of the invention disclosed and claimed in application Ser. No. 10/611,696 filed into U.S. Patent and Trademark Office on Jul. 1, 2003 in the name of Budimir S. Drakulic as a sole inventor and assigned of record to the assignee of record of this application. The amplifier 100 includes a pair of electrodes 112 and 114 each of which is suitably attached to the patient's skin at a selective position on the patient's body. The electrodes 112 and 114 preferably have an identical construction. The electrode 112 is positioned at a selective position on the skin of the patient's body to produce signals related to the functioning characteristics of an organ in the patient's body. The organ may illustratively be the patient's heart, brain, stomach or intestines. The electrode 114 is positioned on the skin of the patient's body at a position displaced from the selective position to provide reference signals. The difference between the signals at the electrodes 112 and 114 represents the functioning characteristics of the selected one of the patient's organs such as the patient's heart.

The signals on the electrode 112 are introduced to an input terminal of an amplifier generally indicated at 116. The amplifier 116 also has a second input terminal which is connected to the output of the amplifier. In this way, the amplifier acts as a unity gain. The amplifier 116 may be purchased as an OPA 129 amplifier from Texas Instruments which is located in Dallas, Texas. The OPA 129 amplifier was originally provided by the Burr Brown Company which was located in Phoenix, Ariz. and which was acquired by Texas Instruments. In like manner, the signals from the electrode 114 are introduced to an input terminal of an amplifier, generally indicated at 118, which may be identical to the amplifier 118 has an input terminal which is connected to the output terminal of the amplifier to have the amplifier act as a unity gain.

Resistors 120 and 122 respectively extend from the output terminals of the amplifiers 116 and 118. The resistor 120 is connected to first terminals of capacitors 124 and 126. The second terminal of the capacitor 124 receives a reference potential such as ground. A connection is made from the resistor 122 to the second terminal of the capacitor 126 and to a first terminal of the capacitor 130, the second terminal of which is provided with the reference potential such as ground. The resistors 120 and 122 may have equal values and the capacitors 124 and 130 may also have equal values.

One terminal of a resistor 132 is connected to the terminal common to the capacitors 124 and 126. The other terminal of the resistor 132 has a common connection with a first input terminal of an amplifier 134. In like manner, a resistor 136 having a value equal to that of the resistor 132 is connected at one end to the terminal common to the capacitors 126 and 130 and at the other end to a second input terminal of the amplifier 134.

Since the amplifiers 116 and 118 have identical constructions, they operate to provide signals which represent the difference between the signals on the electrodes 112 and 114. This indicates the functioning of the patient's organ which is being determined by the amplifier system 110. Although the electrodes 112 and 114 are displaced from each other on the skin of the patient's body, they tend to receive the same noise signals. As a result, the difference between the signals on the output terminals of the amplifiers 116 and 118 results in only a limited amount of noise.

The electrodes 112 and 114 respectively provide an impedance as high as of approximately $10^6$ ohms to the amplifiers 116 and 118. Each of the amplifiers 16 and 18 respectively provides an input impedance of approximately $10^{15}$ ohms. This impedance is so large that it may be considered to cause each of the amplifiers 116 and 118 to operate as if it has an open circuit at its input. The output impedance of each of the amplifiers 116 and 118 is approximately 50 ohms to 75 ohms.

Because of the effective open circuit at the input of each of the amplifiers 116 and 118, the output signal from each of the amplifiers 116 and 118 corresponds to the input signal to the amplifiers and does not have any less magnitude compared to the amplitude of the input signal to the amplifier. This is important in view of the production of signals in the microvolt or millivolt region in the electrodes 112 and 114.

The capacitors 124, 126 and 130 and the resistors 120 and 122 provide a low-pass filter and a differential circuit and operate to eliminate the noise on the electrodes 112 and 114. The capacitors 124, 126 and 130 also operate to provide signals which eliminate the commonality between the signals in the electrodes 112 and 114 so that only the signals individual to the functionality being determined relative to the selected organ in the patient's body remain. The capacitors 124, 126 and 130 operate as a low pass filter and pass signals in a range to approximately one kilohertz (1 KHz). The signals having a frequency above approximately one kilohertz (1 KHz) are attenuated.

The amplifiers 116 and 118 are identical. Because of this, a description of the construction and operation of the amplifier 116 will apply equally as well to the amplifier 118. The amplifier 116 is shown in detail in FIG. 6. It is manufactured and sold by Texas Instruments ("TI") in Dallas, Tex. and is designated by TI as the OPA 129 amplifier.

Figure 8:
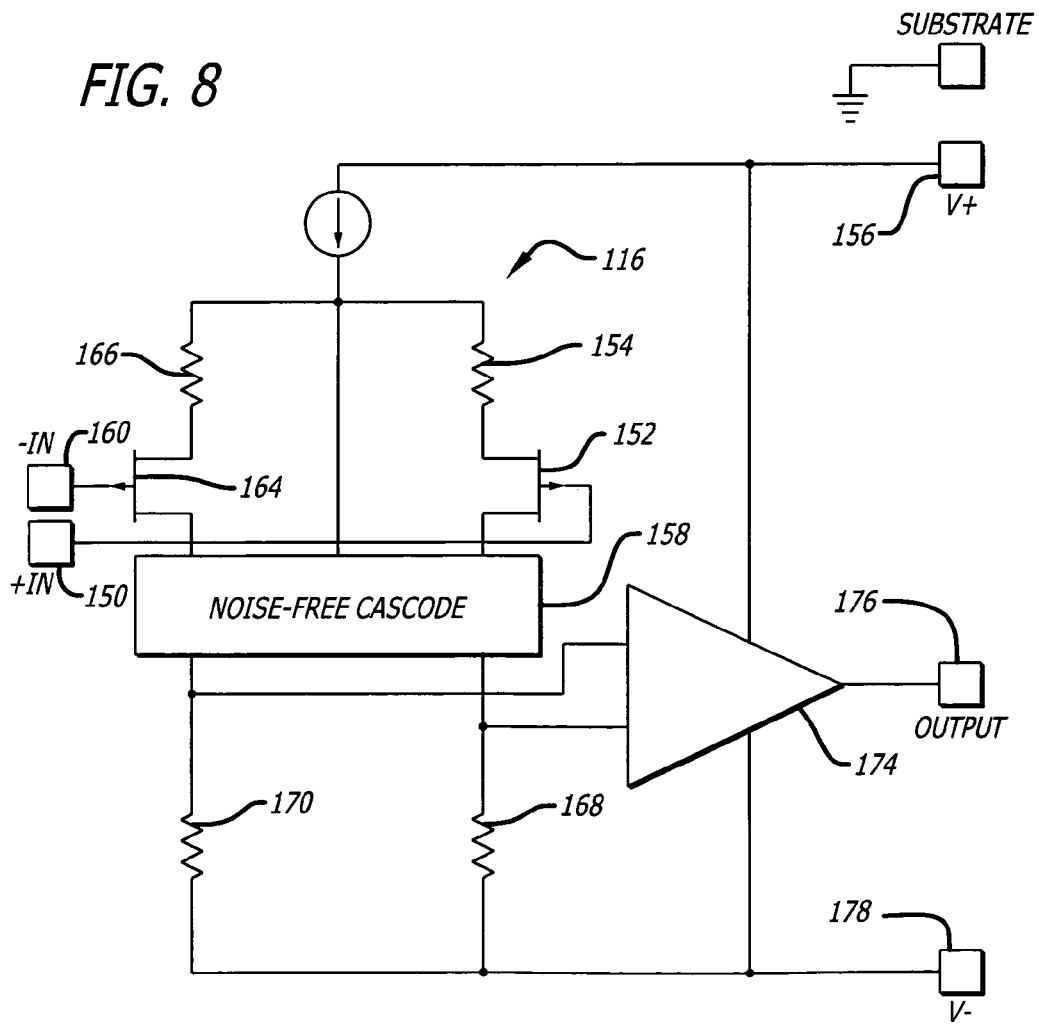
FIG. 8 is a circuit diagram in additional detail of each of the amplifiers included in the amplifier system shown in FIG. 7.

As shown in FIG. 8, the amplifier 116 includes an input terminal 150 which receives the signals at the electrode 112 and introduces these signals to the gate of a transistor 152. The source of the transistor 152 receives a positive voltage from a terminal 156 through a resistor 154. The emitter of the transistor 152 is common with an input terminal in a noise free cascode 158.

Another terminal 160 receives the signals on the electrode 114 and introduces these signals to a gate of a transistor 164. A connection is made from the source of the transistor 164 10 to one terminal of a resistor 166, the other terminal of which receives the voltage from the terminal 156. The emitter of the transistor 164 is common with an input terminal in the noise-free cascode 158. The resistor 166 has a value equal to that of the resistor 154 and the transistors 152 and 164 have identical characteristics.

First terminals of resistors 168 and 170 having equal values are respectively connected to output terminals in the noise-free cascode 158 and input terminals of an amplifier 174. The amplifier 74 provides an output at a terminal 176. The output from the terminal 176 is introduced to the input terminal 160. The amplifier 174 receives the positive voltage on the terminal 156 and a negative voltage on a terminal 178.

Connections are made to the terminal 178 from the second terminals of the resistors 168 and 170.

The transistors 152 and 164 operate on a differential basis to provide an input impedance of approximately $10^{15}$ ohms between the gates of the transistors. The output impedance from the amplifier 116 is approximately fifty (50) ohms to seventy-five (75) ohms. Because of the high input impedance of approximately $10^{15}$ ohms, the amplifier 116 provides the equivalent of an open circuit at its input. This causes substantially all of the voltage applied to the input terminal 150 to be provided at the output of the amplifier 116. This is facilitated by the low impedance of approximately 50 ohms (50 ohms) to seventy-five (75) ohms at the output of the amplifier 116. This voltage has characteristics corresponding to the characteristics of the voltage at the electrode 112.

The output signals from the amplifiers 116 and 118 are respectively introduced to the terminal common to the capacitors 124 and 126 and to the terminal common to the capacitors 126 and 130. The capacitors 124, 126 and 130 operate as a low-pass filter to remove noise and to provide an output signal representing the difference between the signals on the electrodes 112 and 114.

The capacitors 124, 126 and 130 correspond to the capacitors C2, C1 and C3 in a low pass filter 176 in application Ser. No. 10/293,105 filed on Nov. 13, 2002 in the USPTO and assigned of record to the assignee of record in this application. The capacitors C2, C1 and C3 in application Ser. No. 10/293,105 are included in the low pass filter 76 in FIG. 8-1 (also shown in FIG. 4) of such application. The low pass filter 76 eliminates noise and passes signals through a frequency range to approximately one kilohertz (1 KHz). If any further information may be needed concerning the construction and operation of the low pass filter, reference may be made to co-pending application Ser. No. 10/293,105 to obtain this information.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

We claim:

1. In combination for producing signals indicative of body characteristics of a patient,
   a first material having properties of generating heat when exposed to air and becoming porous when heated, and
   a second material having properties of conducting heat and electricity,
   the first material being constructed to be disposed on the patient's skin to become heated and to heat the patient's skin when the first material becomes exposed to air,
   the patient's skin having properties of becoming porous when heated,
   the first material being constructed to be attached to the patient's skin to become porous and heat the patient's skin and to open pores in the patient's skin, when heated, for passage of ions through the opened pores in the patient's skin and through the first material to obtain a generation of an electrical current in the second material.

2. In a combination as set forth in claim 1 wherein
   the first material is wrapped to prevent the first material from being exposed to the air and wherein
   the first material is unwrapped to expose the first material to the air when it is desired to produce a signal indicative of the body characteristics of the patient.

3. In a combination as set forth in claim 2 wherein
   the second material constitutes a thin film which is attached to the first material for converting the ions passing through the first material to an electron current representing the patient's body characteristics and which extends to a terminal for passing the signals from the patient's body and wherein
   the first material produces a substantially constant temperature for an extended period of time when exposed to air and wherein
   the temperature of the first material instantaneously rises to a particular value when exposed to air and thereafter remains at the particular value for an extended period of time wherein
   the particular temperature is dependent upon the amount of the first material exposed to the air and wherein
   the first material is formed from a mixture of activated carbon, iron powder, sawdust, sodium chloride and water and wherein
   the activated carbon, iron powder, sawdust, the sodium chloride and the water are respectively disposed on the mixture in the ratio of approximately 5:16:3:2: and 6.

4. In a combination as set forth in claim 3 wherein
   openings are provided in the first material to expose the first material to air to obtain an oxidation of the first material and wherein
   openings are provided in the second material at the positions of the openings in the first material to provide for the passage of air to the first material.

5. In a combination as set forth in claim 1 wherein
   the second material constitutes a thin film which is attached to the first material for converting the ions passing through the first material to an electron current representing the patient's body characteristics and which extends to a terminal for passing the signals from the patient's body.

6. In a combination as set forth in claim 1 wherein
   the first material produces a substantially constant temperature for an extended period of time when exposed to air.

7. In a combination as set forth in claim 1 wherein
   the temperature of the first material instantaneously rises to a particular value when exposed to air and thereafter remains at the particular value for an extended period of time.

8. In a combination as set forth in claim 7 wherein
   the particular temperature is dependent upon the amount of the first material exposed to the air.

9. In a combination as set forth in claim 1 wherein
   the first material is formed from a mixture of activated carbon, iron powder, sawdust, sodium chloride and water.

10. In a combination as set forth in claim 9 wherein
    the activated carbon, iron powder, sawdust, the sodium chloride and the water are respectively disposed on the mixture in the ratio of approximately 5:16:3:2: and 6.

11. In a combination as set forth in claim 1 wherein
    openings are provided in the first material to expose the first material to air to obtain an oxidation of the first material and wherein
    openings are provided in the second material at the positions of the openings in the first material to provide for the passage of air to the first material.

12. In a combination for producing signals indicative of body characteristics of a patient at a particular position,
    a first material having characteristics of being oxidized and becoming porous when exposed to air to generate heat at a particular temperature as a result of the air exposure and to expose the pores of the patient's skin and the first material for the passage of ions through the patient's skin and the first material at a particular position on the patient's body, a wrapper disposed around the first material to prevent the first material from being exposed to air and from being oxidized at the particular position on the patient's body, and a second material having characteristics of electrical and heat conductivity, the second material having first and second surfaces and being juxtaposed to the first material at the first surface and being operative to convert the flow of the ions through the patient's skin and the first material to an electrical signal when the first material becomes unwrapped from the wrapper and wherein at least a portion of the wrapper is removable from the first material to expose the first material to air at the particular position on the patient's body.

13. In a combination as set forth in claim 12 wherein the heat generated by the first material, when exposed to air, produces pores in the patient's skin and the first material to pass ions from the patient's body through the first material to generate a signal in the second material.

14. In a combination as set forth in claim 13 wherein the second material constitutes a thin strip of a material having heat-conductive and electrically conductive properties and wherein an amplifier is connected to the second material and is constructed to amplify the signals on the second material without affecting the characteristics of the signal in the second material and without producing noise in the amplified signal and wherein the first material has characteristics of becoming oxidized when exposed to air and of producing a substantially constant voltage during oxidation when it is exposed to the air and wherein the substantially constant voltage produced by the first material is dependent upon the amount of the material exposed to the air when the first material is unwrapped from the wrapper.

15. In a combination as set forth in claim 12 wherein the second material constitutes a thin strip of a material having heat-conductive and electrically conductive properties to produce an electrical signal.

16. In a combination as set forth in claim 12 wherein an amplifier is connected to the second material and is constructed to amplify the signal on the second material without affecting the characteristics of the signal in the second material and without producing noise in the amplified signal.

17. In a combination as set forth in claim 12 wherein the first material has characteristics of becoming oxidized when exposed to air and of producing a substantially constant voltage during oxidation when it is exposed to the air.

18. In a combination as set forth in claim 17 wherein the substantially constant voltage generated by the first material is dependent upon the amount of the material exposed to the air when the first material is unwrapped from the wrapper.

19. A method of producing signals having characteristics indicative of body characteristics of a patient at a particular position on the patient's body, including the steps of:

providing a chadd for disposition on the patient's skin at the particular position on the patient's body, the chadd having properties of opening pores in the chadd when the chadd becomes heated, and generating heat in the chadd to open the pores in the patient's skin and the chadd at the particular position and provide for the passage of ions through the pores in the patient's skin and pores in the chadd, and providing an electrode on the chadd to convert the ions to an electrical signal.

20. A method as set forth in claim 19 including the step of:

amplifying the signal produced at the electrode without affecting the characteristics of the signal and without producing noise.

21. A method as set forth in claim 19 wherein the chadd is constructed to be heated instantaneously to a particular temperature and to be maintained at the particular temperature for a particular period of time.

22. A method as set forth in claim 19 wherein the chadd is constructed to be disposed on the patient's skin at the particular position to generate, when exposed to air, heat at a substantially constant temperature dependent upon the amount of the material that is exposed to the air.

23. A method as set forth in claim 19 wherein the chadd is formed from a mixture of activated carbon, iron powder, sawdust, sodium chloride and water.

24. A method as set forth in claim 23 wherein the activated carbon, the iron powder, the sawdust, the sodium chloride, and the water are respectively disposed in the mixture in the ratio of approximately 5:16:3:2: and 6.

25. A method of producing signals having characteristics indicative of body characteristics of a patient at a particular position on a patient's body, including the steps of:

providing a chadd having properties of becoming oxidized when exposed to air, the chadd being wrapped to prevent the chadd from being oxidized, unwrapping the chadd to provide for the oxidation of the chadd, disposing the unwrapped chadd at the particular position on the patient's body, exposing the unwrapped chadd to air to provide for a heating of the chadd and the patient's skin and an opening of pores in the chadd and the patient's skin and a flow of ions in the skin through the pores in the patient's skin and the chadd, and providing the unwrapped chadd on the patient's skin to heat the patient's body at the particular position and open the pores in the patient's skin for the flow of ions through the pores in the patient's skin at the particular position, and providing a layer on the chadd to convert the flow of ions through the patient's skin and the chadd to an electrical signal.

26. A method as set forth in claim 25 wherein when the chadd is unwrapped and exposed to air, the chadd becomes heated to a particular temperature dependent upon the portion of the chadd that is exposed to the air when the chadd is unwrapped.

27. A method as set forth in claim 25 wherein the chadd has characteristics of producing a substantially constant temperature for an extended period of time, the substantially constant temperature being dependent upon the portion of the chadd that is exposed to the air when the chadd becomes unwrapped.

28. A method as set forth in claim 25 wherein
the chadd has characteristics of becoming heated substantially instantaneously to a substantially constant temperature by oxidation of the chadd when the chadd becomes unwrapped.

29. A method as set forth in claim 25 wherein
the chadd is formed from a mixture of activated carbon, iron powder, sawdust, sodium chloride and water.

30. A method as set forth in claim 29 wherein
the activated carbon, the iron powder, the sawdust, the sodium chloride and the water are respectively disposed in the mixture in the ratio of approximately 5:16:3:2: and 6.

31. A method as set forth in claim 25 wherein
the chadd has characteristics of producing a substantially constant temperature for an extended period of time, the substantially constant temperature being dependent upon the portion of the chadd that is exposed to the air when the chadd becomes unwrapped and wherein
the chadd has characteristics of becoming heated substantially instantaneously to the substantially constant temperature by oxidation of the chadd when the chadd becomes unwrapped and wherein
the chadd is formed from a mixture of activated carbon, iron powder, sawdust, sodium chloride and water and wherein
the activated carbon, the iron powder, the sawdust, the sodium chloride and the water are respectively disposed in the mixture in the ratio of approximately 5:16:3:2: and 6.

32. A method of producing signals having characteristics indicative of body characteristics of a patient at a particular position on the patient's body, including the steps of:
providing a chadd at the particular position on the patient's body, the chadd having characteristics of becoming porous and of producing pores in the patient's skin and of passing ions from the pores in the patient's skin through the pores in the chadd, when the chadd is heated,
providing a layer on the chadd with characteristics of converting the ions in the pores in the chadd to an electrical signal, and
providing an electrical lead on the layer with characteristics of passing the electrical signal converted by the layer.

33. A method as set forth in claim 32 wherein
the electrical lead extends to a terminal and wherein
an amplifier constructed to be connected to the terminal amplifies the electrical signal without affecting the characteristics of the signal and without generating noise.

34. A method as set forth in claim 32 wherein
the layer is formed from a material selected from the group consisting of silver and silver chloride and wherein
the chadd is formed from a mixture constituting a mixture of activated carbon, iron powder, sawdust, sodium chloride and water.

35. A method as set forth in claim 32 wherein
the total thickness of the chadd, the layer and the electrical lead is no greater than approximately two millimeters (2 mm).

36. A method as set forth in claim 32 wherein
the electrical lead is formed from a material selected from the group consisting of carbon and a conductive plastic including polyurethane.

37. A method as set forth in claim 32 wherein
the layer is formed from a material selected from the group consisting of silver and silver chloride and wherein
the chadd is formed from a mixture constituting a mixture of activated carbon, iron powder, sawdust, sodium chloride and water and wherein
the total thickness of the chadd, the layer and the lead is no greater than approximately two millimeters (2 mm) and wherein
the electrical lead is formed from a material selected from the group consisting of carbon and a conductive plastic including polyurethane.

38. A method as set forth in claim 37 wherein
the chadd is formed from a material having properties of becoming oxidized when exposed to air.

39. A method as set forth in claim 32 wherein
the chadd is formed from a mixture of activated carbon, iron powder, sawdust, sodium chloride and water.

40. A method as set forth in claim 39 wherein
the activated carbon, the iron powder, the sawdust, the sodium chloride and water are disposed in the mixture in the ratio of approximately 5:16:3:2:6.

41. A method as set forth in claim 32 wherein
the chadd is formed from a material having properties of becoming oxidized when exposed to air.

42. In combination for producing signals indicative of body characteristics of a patient at a particular position in the patient's body,
a chadd constructed to be disposed on the patient's skin at the particular position in the patient's body and constructed to be oxidized, and to provide ions in the oxidation, when exposed to air,
a layer of a material disposed on the chadd and having properties of producing electrons responsive to the ions from the chadd, and
an electrical lead disposed on the layer and having properties of producing an electrical signal in response to the electrons produced in the layer.

43. In a combination as set forth in claim 42 wherein
the electrical lead is formed from an electrically conductive material and wherein the electrically conductive material extends to a terminal and wherein
an amplifier connected to the terminal has properties of amplifying the electrical signal without affecting the characteristics of the signal and without producing noise.

44. In a combination as set forth in claim 42 wherein
the chadd has properties of becoming heated when oxidized and of becoming porous when heated and of heating the skin contiguous to the chadd and producing pores in the skin upon the heating of the skin and of providing for the flow of ions through the pores in the skin and the chadd upon the heating of the skin and the chadd.

45. In a combination as set forth in claim 44 wherein
the layer of the material on the chadd has properties of reacting chemically with the ions flowing through the skin and the chadd to produce electrons in the layer and to provide for the production of the electrical signal in the electrical lead and wherein
the electrical lead is formed from an electrically conductive material and wherein the electrically conductive material extends to a terminal and wherein
an amplifier connected to the terminal has properties of amplifying the electrical signal without affecting the characteristics of the signal and without producing noise.

46. In a combination as set forth in claim 45 wherein
the chadd is formed from a mixture of activated carbon, iron powder, sawdust, sodium chloride and water.

47. In a combination as set forth in claim 45 wherein
the chadd is formed from a mixture of activated carbon, iron powder, sawdust, sodium chloride and water and wherein
the electrical lead is formed from an electrically conductive material selected from the group consisting of electrically conductive carbon and a electrically conductive plastic including conductive polyurethane.

48. In a combination as set forth in claim 44 wherein
the electrical lead is formed from an electrically conductive material selected from the group consisting of conductive carbon and a conductive plastic including conductive polyurethane.

49. In a combination as set forth in claim 42 wherein
the layer of the material on the chadd has properties of reacting chemically with the ions flowing through the skin and the chadd to produce electrons in the layer and to provide for the production of the electrical signal in the electrical lead.

50. In a combination as set forth in claim 42 wherein
the chadd is formed from a mixture of activated carbon, iron powder, sawdust, sodium chloride and water and wherein
the electrical lead is formed from an electrically conductive material selected from the group consisting of electrically conductive carbon and a conductive plastic including electrically conductive polyurethane.

51. In combination for producing signals indicative of body characteristics of a patient at a particular position in the patient's body,
a chadd constructed to be disposed on the patient's skin at the particular position in the patient's body and constructed to be oxidized when exposed to air, the chadd having openings for exposure to air to generate heat for increasing the temperature of the chadd, when the chadd is exposed to air, for making the chadd and the patient's skin porous at the particular position to obtain the flow of ions in the patient's body through the patient's skin and the chadd at the particular position, and
a layer of an electrically conductive material on the chadd for converting the ions to electrons indicative of the ions passing to the layer.

52. In a combination as set forth in claim 51 wherein
the layer is formed from an electrically conductive material including silver and silver chloride.

53. In a combination as set forth in claim 52 wherein
an amplifier is responsive to a signal provided by the electrons for amplifying the signal without affecting the characteristics of the signal and without producing noise and wherein
the chadd is formed from a mixture of activated carbon, iron powder, sawdust, sodium chloride and water.

54. In a combination as set forth in claim 53 wherein
the activated carbon, iron powder, sawdust, sodium chloride and water are disposed in the chadd in the ratios of 5:16:3:2:6.

55. In a combination as set forth in claim 51,
an amplifier responsive to a signal provided by the electrons for amplifying the signal without affecting the characteristics of the signal and without producing noise.

56. In a combination as set forth in claim 51 wherein
the chadd is formed from a mixture of activated carbon, iron powder, sawdust, sodium chloride and water.

* * * * *

UNITED STATES PATENT AND TRADEMARK OFFICE
CERTIFICATE OF CORRECTION

| | | |
|---|---|---|
| PATENT NO. | : 7,299,083 B2 | Page 1 of 1 |
| APPLICATION NO. | : 11/008681 | |
| DATED | : November 20, 2007 | |
| INVENTOR(S) | : Budimir Drakulic | |

It is certified that error appears in the above-identified patent and that said Letters Patent is hereby corrected as shown below:

Column 2, line 32, change "-the-patient's" to --the patient's--.
Column 4, line 15, delete "at".
Column 6, line 64, change "74" to --174--.

Signed and Sealed this

First Day of July, 2008

JON W. DUDAS
*Director of the United States Patent and Trademark Office*